United States Patent [19]

Levitt et al.

[11] 4,362,549
[45] Dec. 7, 1982

[54] METHOD OF INCREASING SUGAR CONTENT IN SUGARCANE AND SORGHUM

[75] Inventors: George Levitt, Wilmington, Del.; William F. Smith, III, Elkton, Md.

[73] Assignee: E. I. Du Pont de Nemours and Company, Wilmington, Del.

[21] Appl. No.: 234,235

[22] Filed: Feb. 13, 1981

[51] Int. Cl.$^3$ ............................................. A01N 43/54
[52] U.S. Cl. ............................................. 71/92; 71/93
[58] Field of Search ................................ 71/92, 103

[56] References Cited

U.S. PATENT DOCUMENTS

| | | | |
|---|---|---|---|
| 3,525,603 | 8/1970 | Hamm | 71/103 |
| 3,556,764 | 1/1971 | Hamm | 71/103 |
| 4,214,890 | 7/1980 | Levitt | 71/92 |
| 4,238,621 | 12/1980 | Levitt | 71/92 |
| 4,239,526 | 12/1980 | Siemer | 71/92 |

OTHER PUBLICATIONS 998702 07001965 GBX 71 103
Nickell et al., "Effects of Chemicals, etc;", (1965) Haw. Sug. Rpts., pp. 152–166 (1965).

Primary Examiner—Glennon H. Hollrah

[57] ABSTRACT

The application of certain sulfonylurea compounds to sugarcane and sorghum increases their sugar content. These compounds have the formula:

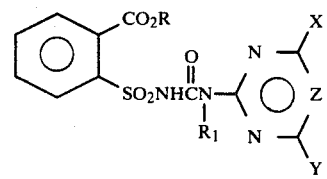

wherein
R is $C_1$–$C_4$ alkyl, $C_3$–$C_4$ alkenyl, $CH_2CH_2OCH_3$ or $CH_2CH_2Cl$;
$R_1$ is H or $CH_3$;
X is $CH_3$, $OCH_3$, $OC_2H_5$ or $CH_2OCH_3$;
Y is $CH_3$ or $OCH_3$; and
Z is CH or N; or an agriculturally acceptable salt thereof.

4 Claims, No Drawings

METHOD OF INCREASING SUGAR CONTENT IN SUGARCANE AND SORGHUM

BACKGROUND OF THE INVENTION

1. Field of the Invention

This invention relates to methods for increasing the sugar content of sugarcane and sorghum.

2. Prior Art

The primary purpose for growing sugarcane and sweet sorghum is the production of sugars, principally sucrose. All genetic improvements in crop varieties and innovations in fertilization, pest control and cultural practices are developed to produce highest yields of sugars per hectare with the least expenditure of energy and manpower. Additional ways to increase sugar yields are to induce the plant to either produce more sugars or to hold on to those already produced.

Vigorous vegetative growth uses up sugars because it requires high rates of metabolism. Squandering sugars by excessive growth near normal cane harvest time can be partially controlled by withholding water or by limiting nitrogen availability. These methods of ripening are not reliable because they are difficult to control. A more controllable, predictable method is to use specific chemical growth modifier sprays that will inhibit vegetative growth and allow sugars to build up in the stalks. Chemicals that will cause sucrose to accumulate are called cane ripeners or sugar enhancers.

During the past decade considerable research effort has been expended in the sugarcane industry to develop chemical sugar enhancers. N,N-bis-phosphonomethylglycine has emerged as a practical treatment in most cane growing areas of the world, particularly in high rainfall areas where natural ripening cannot be induced by withholding water. Newer experimental ripeners are being developed, which will have utility under wider rainfall conditions.

It has been estimated that about 5 million hectares of sugarcane are amenable to the application of chemical ripeners.

A wide variety of sulfonylurea compounds are known as broad spectrum herbicides and plant growth regulants. For example, U.S. Pat. Nos. 4,127,405, issued Nov. 28, 1978 and 4,169,719, issued Oct. 2, 1979, describe a number of triazine and pyrimidine compounds respectively for the above uses. Compounds useful in the present invention are described in published European Patent No. 7687, published on Feb. 6, 1980.

SUMMARY OF THE INVENTION

According to the present invention there is provided a method for increasing the sugar content of sugarcane and sorghum comprising: applying to the sugarcane and sorghum prior to harvest an effective amount of a compound of the formula:

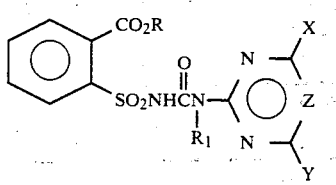

(I)

wherein

R is $C_1$-$C_4$ alkyl, $C_3$-$C_4$ alkenyl, $CH_2CH_2OCH_3$ or $CH_2CH_2Cl$;

$R_1$ is H or $CH_3$;

X is $CH_3$, $OCH_3$, $OC_2H_5$ or $CH_2OCH_3$;

Y is $CH_3$ or $OCH_3$; and

Z is CH or N;

or an agriculturally acceptable salt thereof.

DETAILED DESCRIPTION OF THE INVENTION

It has been discovered that the compounds of Formula I above when applied at an effective amount to sugarcane and sorghum prior to harvest result in an increase in the sugar or sucrose content of the harvested crops. Preferred compounds in increasing order for their activity are those compounds of Formula I where:

(a) $R_1$ is H;

(b) X is $CH_3$ or $OCH_3$; and (c) R is $CH_3$ or $CH_2CH=CH_2$.

Specifically preferred compounds are:

(a) Methyl 2-[[(4,6-dimethylpyrimidin-2-yl)aminocarbonyl]aminosulfonyl]benzoate;

(b) Methyl 2-[[(4-methoxy-6-methyl-1,3,5-triazin-2-yl)aminocarbonyl]aminosulfonyl]benzoate; and (c) (1-propenyl) 2-[[(4,6-dimethoxyprimidin-2-yl)aminocarbonyl]aminosulfonyl]benzoate.

The preparation of these compounds and their formulation are described in the aforesaid published European Patent No. 7687 and the disclosures therein on preparation and formulation are hereby incorporated by reference.

It is preferred that a compound of Formula I be applied to the sugarcane or sorghum about 2-8 weeks prior to normal harvest of the crop. Such an application results in an increase in the sugar content of the expressed plant juice obtained. While the physiological mechanism involved in their increase in sugar content is not fully understood, it is apparent that the compounds of this invention redirect the carbohydrate metabolism in the plant in such a way as to increase the sugar level in the plant juices.

The precise amount of a compound of Formula I to use for optimum sugar increase will vary according to the maturity and physiological condition of the crop and the time elapsing after treatment until harvest. In general, the compounds of this invention are used at levels of about 0.001 to 5 kg/ha with a preferred range being about 0.002 to 2 kg/ha. The higher rates may in general be applied to more mature plants closer to the time of harvest.

The sugar enhancing activity of these compounds was discovered in greenhouse tests and further substantiated in field evaluation. These tests and the results obtained are described in the following examples where parts and percentages are by weight and where compound 1 has the formula:

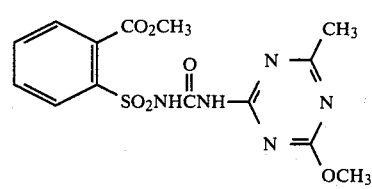

Compound 1 and compound 2 has the formula:

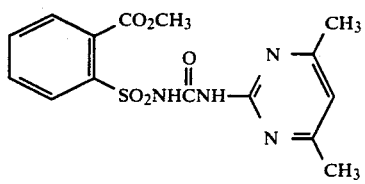

Compound 2

EXAMPLE 1

Sugarcane nodal stem sections were planted in greenhouse soil contained in 10-inch diameter plastic bulb pans. The developing plants were watered, fertilized and thinned to 3 plants per pot as needed for about 6 months at which time the plants were from 8 to 10 feet tall. Selected rates of compound 2 were sprayed on the foliage of the upper one-third of the plants from an aqueous formulation at a volume rate of about 250 l/ha. Four weeks after treating, the sugarcane stalks were cut-off at the soil surface, stripped of leaves and run through a roller cane press. The percent soluble solids (sucrose) was determined in the expressed plant juice as recorded in Table I.

TABLE I

| Compound | Treatment Rate kg/ha | Percent Soluble Solids Replications | | | |
|---|---|---|---|---|---|
| | | A | B | C | Mean |
| 2 | .004 | 15.5 | 15.5 | 15.0 | 15.3 |
| 2 | .016 | 15.5 | 15.5 | 17.0 | 16.0 |
| 2 | .064 | 16.5 | 16.0 | 16.5 | 16.3 |
| Diluent Control | — | 12.0 | 12.5 | 13.0 | 12.5 |

EXAMPLE 2

Sorghum, Sugar Drip variety, was seeded in Fallsington silt loam soil contained in 6-inch plastic pots. After emergence, the plants were thinned to a single plant per pot and grown under normal greenhouse conditions for 8 weeks at which time the flag leaf had emerged, indicating that seed head emergence was imminent. The plants were then sprayed with selected concentrations of compounds 1 and 2 from an aqueous formulation at a volume rate of 560 l/ha. Four weeks after treating, the sorghum stalks were pressed to extract the juice and the percent soluble solids (sucrose) was determined. Results of these determinations are recorded in Table II.

TABLE II

| Compound | Rate kg/ha | % Soluble Solids |
|---|---|---|
| 1 | .008 | 16.0 |
| 1 | .031 | 15.0 |
| 1 | .125 | 15.0 |
| 2 | .008 | 10.0 |
| 2 | .031 | 10.0 |
| 2 | .125 | 10.0 |
| Diluent Control | — | 13.2 |

EXAMPLE 3

Sugarcane (Louisiana variety) was transplanted into 3-gallon plastic pots and grown in the greenhouse for about 7 weeks. Three stalks were maintained in each pot. After the 7 week period, when the sugarcane was well established, selected rates of compound 1 and compound 2 were sprayed from an aqueous formulation onto the foliage. After 5 weeks, the sugarcane was cut-off at the soil surface, stripped of leaves and the stalks were passed through a roller press to extract the juice. The percent soluble solids (sucrose) was determined in the expressed juice with a refractometer as recorded in Table III.

TABLE III

| Compound | Treatment Rate kg/ha | Mean % Soluble Solids | |
|---|---|---|---|
| | | % | % of Untreated Control |
| Series A | | | |
| 1 | .062 | 16.1 | 137.6 |
| 1 | .25 | 17.1 | 146.2 |
| 2 | .004 | 17.8 | 152.2 |
| 2 | .016 | 19.5 | 166.7 |
| 2 | .062 | 19.9 | 170.1 |
| Untreated Control | — | 11.7 | 100 |
| Series B | | | |
| 1 | .016 | 17.4 | 136.0 |
| 1 | .062 | 18.4 | 143.8 |
| 1 | .25 | 17.3 | 135.2 |
| 2 | .004 | 17.4 | 136.0 |
| 2 | .016 | 19.0 | 148.5 |
| 2 | .062 | 18.0 | 140.7 |
| Untreated Control | — | 12.8 | 100 |

EXAMPLE 4

Sugardrip sweet sorghum was grown under standard field culture for two months. When most of the seedheads had emerged and were starting to shed pollen, the top one-third of the plants were sprayed with selected rates of compound 2 from an aqueous formulation on single row plots five meters long with untreated buffer rows between treated plots. Four weeks after treating, a three meter section of each plot was harvested. The sorghum plants were stripped of their leaves and the remaining stalks were run through a roller press to extract the juice. Percent soluble solids (sucrose) and mean sugar yields were determined as recorded in Table IV.

TABLE IV

| Compound | Treatment Rate kg/ha | Results as % of Control | |
|---|---|---|---|
| | | % Soluble Solids | % Sugar Yields |
| 2 | .0015 | 107 | 101 |
| 2 | .006 | 109 | 125 |
| 2 | .025 | 110 | 116 |
| Control | — | (15.2%) | (952g)* |

*grams per 3 meters of row.

EXAMPLE 5

Plots 15 meters long and 4 meters wide in field grown sugarcane in Hawaii were sprayed about 8 weeks before harvest with a wettable powder formulation of compound 2 dispersed in water. The sugarcane from these plots was harvested and processed by normal mill procedures. Table V presents the results obtained from treated cane compared with results from cane harvested from untreated plots.

TABLE V

| Compound | Application Rate kg/ha | % Soluble Solids | % Sucrose | % Purity |
|---|---|---|---|---|
| 2 | 0.25 | 16.48 | 14.11 | 85.95 |
| Untreated | — | 13.79 | 10.88 | 78.95 |

What is claimed is:

1. A method for increasing the sugar content of sugarcane and sorghum comprising: applying to the sugarcane or sorghum about 2-6 weeks prior to harvest an effective amount of a compound of the formula:

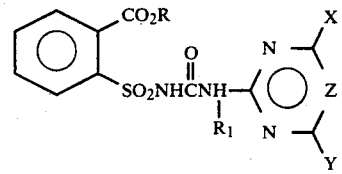

wherein
R is $CH_3$;
$R_1$ is H or $CH_3$;
X is $CH_3$, or $OCH_3$;
Y is $CH_3$ or $OCH_3$; and
Z is CH;
or an agriculturally suitable salt thereof.

2. The method of claim 1 wherein $R_1$ is H.
3. The method of claim 1 wherein the compound is applied at a rate of about 0.002-2 kg/ha.
4. The method of claim 1 wherein the compound is methyl 2-[[4,6-dimethylpyrimidin-2-yl)aminocarbonyl]aminosulfonyl]benzoate.

* * * * *